United States Patent
Pine et al.

(10) Patent No.: US 8,162,219 B2
(45) Date of Patent: Apr. 24, 2012

(54) SYSTEM AND METHOD FOR LOGO IDENTIFICATION AND VERIFICATION

(75) Inventors: Jeffrey A. Pine, Auburn, NY (US); Mo Chen, Liverpool, NY (US)

(73) Assignee: JADAK LLC, North Syracuse, NY (US)

( * ) Notice: Subject to any disclaimer, the term of this patent is extended or adjusted under 35 U.S.C. 154(b) by 0 days.

(21) Appl. No.: 11/971,294

(22) Filed: Jan. 9, 2008

(65) Prior Publication Data

US 2009/0173791 A1    Jul. 9, 2009

(51) Int. Cl.
*G06K 7/10* (2006.01)

(52) U.S. Cl. ........... 235/454; 235/472.01; 382/103; 358/1.14

(58) Field of Classification Search ........... 235/454, 235/472.01; 382/103; 358/1.14
See application file for complete search history.

(56) References Cited

U.S. PATENT DOCUMENTS

| | | | |
|---|---|---|---|
| 7,024,558 B1 * | 4/2006 | Satake | 713/176 |
| 2003/0089764 A1 * | 5/2003 | Meadow et al. | 235/375 |
| 2006/0017959 A1 * | 1/2006 | Downer et al. | 358/1.14 |
| 2006/0045312 A1 * | 3/2006 | Bernstein et al. | 382/103 |
| 2006/0119876 A1 * | 6/2006 | Kenner | 358/1.14 |
| 2006/0131389 A1 * | 6/2006 | Kwon | 235/380 |
| 2007/0065857 A1 * | 3/2007 | Glaser et al. | 435/6 |
| 2007/0252001 A1 * | 11/2007 | Kail et al. | 235/380 |
| 2007/0291988 A1 * | 12/2007 | Karimov et al. | 382/103 |
| 2007/0295812 A1 * | 12/2007 | Mazowiesky et al. | 235/454 |
| 2008/0000966 A1 * | 1/2008 | Keiser | 235/382 |
| 2008/0030798 A1 * | 2/2008 | O'Neil | 358/448 |
| 2008/0215489 A1 * | 9/2008 | Lawson et al. | 705/50 |
| 2008/0296375 A1 * | 12/2008 | Haas et al. | 235/386 |
| 2008/0296393 A1 * | 12/2008 | Jovanovski et al. | 235/472.01 |

* cited by examiner

*Primary Examiner* — Allyson Trail

(74) *Attorney, Agent, or Firm* — David L. Nocilly; Bond Schoeneck & King

(57) ABSTRACT

A system for automatically identifying a logo or trademark applied to a device and verifying that the logo or trademark is acceptably identifies a compatible device. The system uses an optical imager to capture optical images of the target device and a microcontroller interconnected to the imager for processing the optical image to extract image information and verify that the contents of the image reflect the appropriate manufacturer or supplied indicia required by a host device. The decision reached by the microcontroller may be provided externally to a host device, thereby precluding or allowing use of the device, or provided directly to a user via know means, such as a visual display or audible output.

17 Claims, 2 Drawing Sheets

SYSTEM AND METHOD FOR LOGO IDENTIFICATION AND VERIFICATION

BACKGROUND OF THE INVENTION

1. Field of the Invention

The present invention relates to data collection systems and, more specifically, to a system and method of logo identification for verifying the compatibility for medical and other devices.

2. Description of the Related Art

Many medical instruments, such as electrosurgical scalpels, include one or more reusable or disposable medical implements that must be attached to or used in connection with a base unit. Safe operation of such medical devices requires that the authentic implement is attached or interconnected to the corresponding base unit, and that the base unit is properly configured for the safe operation of the particular instrument. In other systems employing a single unit or piece of equipment, it may be important simply to verify the authenticity of a particular instrument or device without regard to whether the instrument is compatible.

Conventional identification method for such systems comprise the addition of distinctive markings, such as dot patterns, to a device or implement that are then recognized by photodiodes interfaced with or included as part of the base unit. While these systems provide basic identification capabilities, they lack sophisticated processing capabilities, provide only rudimentary information to the host unit, may not be easily upgraded in the field, are not always secure (e.g., wrong instrument for wrong application), cannot distinguish between inferior "knock-off" implements that may be unintentionally or intentionally attached to the base unit, such as an implement made by a competing manufacturer, and do not always effectively distinguish between similar implements. In addition, the conventional systems lack any ability to determine the location or orientation of a device based on the orientation and position of an indentifying indicia.

BRIEF SUMMARY OF THE INVENTION

It is therefore a principal object and advantage of the present invention to provide a system and method for ensuring the authenticity of medical devices.

It is an additional object and advantage of the present invention to provide a system and method for ensuring the safety of replacement parts.

It is a further object and advantage of the present invention to provide a system and method for improving the effectiveness of authentication systems.

It is another object and advantage of the present invention to provide a system and method for to determine the proper positioning of an authenticating indicia.

In accordance with the foregoing objects and advantages, the present invention provides a system for identifying manufacturer specific indicia, such as a logo or trademark, that is applied to a device, such as medical implement, and verifying that the appropriate indicia is present on the device. The system comprises an optical imager for capturing optical images of the target device and a microcontroller interconnected to the imager for processing the optical image to extract image information and verify that the contents of the image reflect the appropriate manufacturer or supplied indicia required by a host device. The microcontroller is programmed to process the image information to determine if the requisite indicia is present and, if so, verify that the indicia is acceptable. The decision may then be provided to a host device, such as a medical device, thereby providing a means by which access to the medical device may be controlled. For example, if the proper indicia are not presented to the imager, a control signal may be passed to the host device indicating that the device should not be enabled for use.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 1:
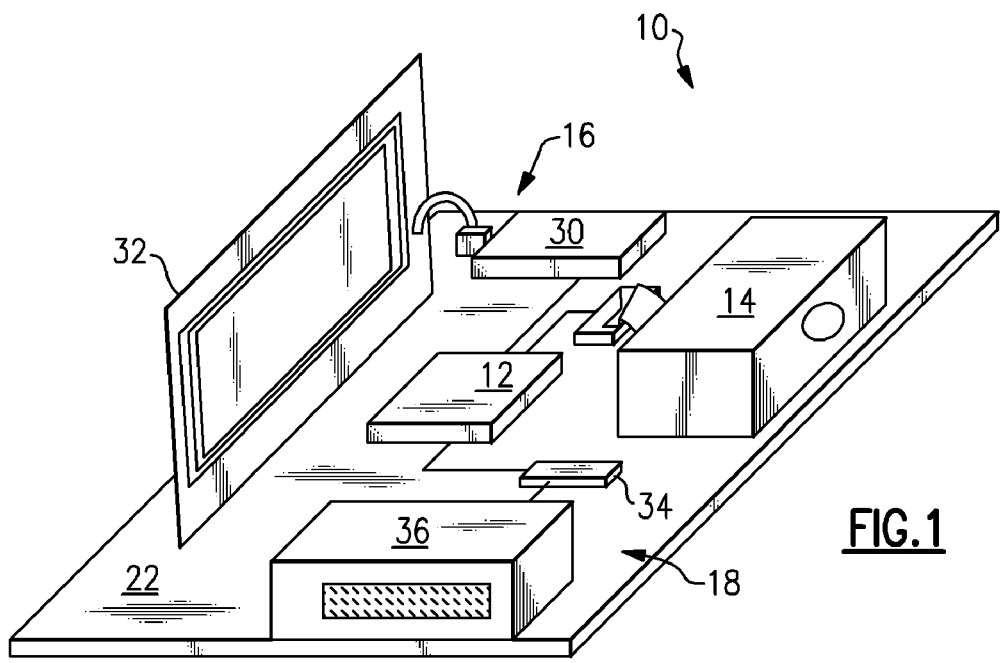
FIG. 1 is a perspective view of an authentication control system according to the present invention.

Referring now to the drawings, wherein like reference numerals refer to like parts throughout, there is seen in FIG. 1 an indicia recognition system 10 according to the present invention. System 10 comprises a microcontroller 12 that is interconnected to a first optical imager 14 and/or an RFID unit 16 to a host interface 18. It should be recognized by those of skill in the art that RFID unit 16 is an optical feature not necessary to the present invention, but which may provide additional benefits and security. System 10 may be arranged on a single printed circuit board 22 and encased as a single unit or housing. Integration of imager 14 and RFID unit 16 through interface 18 allows for combining control of operation of both submodules, such as RFID reading and barcode, through system 10.

Figure 2:
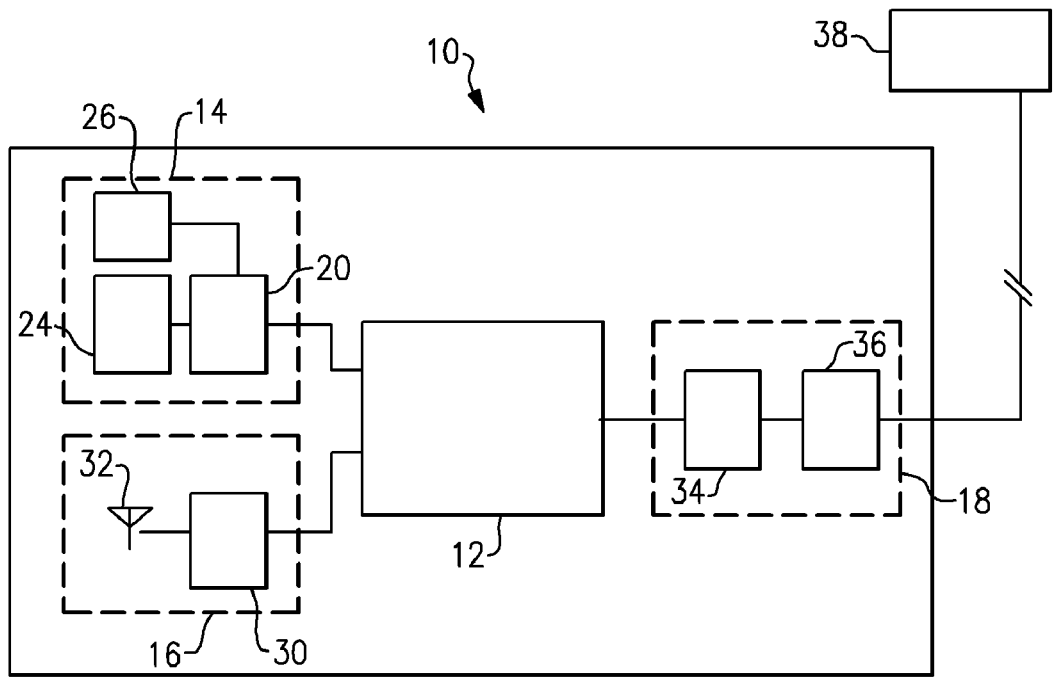
FIG. 2 is a schematic of an authentication control system according to the present invention.

Referring to FIG. 2, optical imager 14 comprises an image engine 20 having image processing circuitry interconnected to microcontroller 12 for omni-directional optical scanning. Image engine 20 controls an image sensor 24, such as a complementary metal oxide semiconductor (CMOS) image sensor, and is capable of capturing two-dimensional images of ID linear barcodes, 2D stacked/matrix barcodes, standard optical character recognition (OCR) fonts, Reduced Space Symbology (RSS) barodes, and postal barcodes, as well as providing image captured images for use in a wide range of applications, such as image and shape recognition, signature capture, image capture, and non-standard optical character recognition.

Imager 14 may comprise, but is not limited to, an IT4X10/80 SR/SF or IT5X10/80 series imager available from Hand Held Products, Inc. of Skaneateles Falls, N.Y. that is capable of scanning and decoding most standard barcodes including linear, stacked linear, matrix, OCR, and postal codes. Specifically, the IT5X10/80 series imager is a CMOS-based decoded output engines that can read 2D codes, and has image capture capabilities sufficient for use with system 10. Imager 14 obtains an optical image of the field of view and, using pre-programmed algorithms in image engine 20, deciphers the context of the image to determine the presence of any decodable barcodes, linear codes, matrix codes, and the like. Image engine 20 may be programmed to perform other image processing algorithms on the image captured by imager 14, such as shape recognition, match filtering, and other high-level processing techniques. Alternatively, a captured image may be processed by microprocessor 12, albeit with a decreased level of performance due to the additional communication time needed to transfer images from image engine 20 to microprocessor 12. Imager 14 further includes an illumination source 26, such as one or more light-emitting diodes (LEDs) of various wavelengths, i.e., colors. Those of skill in the art will instantly recognize that illumination source 26 may be provided as part of imager 14 or as a separate unit depending on the requirements of the particular application.

System 10 may optionally include RFID unit 16 including an RFID transceiver 30 and associated RFID antenna 32 supporting standard RFID protocols, such as the TI Tag-it transponder protocol or ISO 15693. For these protocols, transceiver 30 operates at 13.56 MHz, and may comprise a S6700 Multi-Protocol Transceiver IC available from Texas Instruments of Dallas, Tex. Depending on the application, other frequency transceivers may be more appropriate based on target range, power availability, cost, etc. RFID unit 16 may further include a speaker or LED (not shown) for audibly indicating a successful interrogation of an RFID tag.

Antenna 32 is preferably a loop antenna of various sizes and turns implemented on a printed circuit board and connected to system 10, or a wire loop installed antenna installed directly onto system 10. Antenna 32 may be positioned remotely, thereby reducing the footprint of system 10 using an external connector, such as a MMCX coaxial connector. RFID transceiver 30 may be programmed to interrogate passive or active tags, process signals received from such tags (e.g., analog to digital conversion), and provide the information from the tags to microcontroller 12 for further processing or transmittal to a host computer via interface 18.

Host interface 18 comprises a host transceiver 34 and a host connector 36 for interconnection to a host device 38. Interface 18 may comprise a conventional RS232 transceiver and associated 12 pin RJ style jack. For example, an ADM202EARN available from Analog Devices, Inc. of Norwood, Mass. is a suitable RS-232/V.28 interface device having compliant levels of electromagnetic emissions and immunity. Alternatively, interface 18 may comprise other conventional buses, such as USB, IEEE 1394, I2C, SPI, or PCMCIA, or other connector styles, such as an FFC style to an embedded host or another system 10. Interface 18 may also comprise a wireless transceiver in lieu of connector 36 for wireless communication to a host computer. A Stewart Connector Systems Inc. SS-641010S-A-NF may serve as connector 36 for mating with a Stewart Connector 937-SP-361010-031 matching connector of a host device. Host interface 18 may also comprise a Molex MX52588 connector. Regardless of the type of connector 36 used in connection with system 10, host transceiver 34 is programmed with the applicable protocols for interfacing with a host computer, such as USB, Bluetooth(r), and IrDA protocols. Transceiver 34 may also be programmed to support both non-inverted signal sense and inverted signal sense.

Microcontroller 12 comprises a conventional programmable microprocessor having on-chip peripherals, such as central processing unit, Flash EEPROM, RAM, asynchronous serial communications interface modules, serial peripheral interfaces, Inter-IC Buses, timer modules, pulse modulators with fault protection modules, pulse width modulators, analog-to-digital converters, and digital-to-analog converters. Additionally, the inclusion of a PLL circuit allows power consumption and performance to be adjusted to suit operational requirements. In addition to the I/O ports, dedicated I/O port bits may be provided. Microcontroller 12 may further include an on-chip bandgap based voltage regulator that generates an internal digital supply voltage from an external supply range. Microcontroller 12 preferably comprises a Motorola MC9S12E128.

The functional integration of imager 14 and RFID unit 16 to interface 18 is accomplished by microcontroller 12, which receives and interprets host commands, and then executes the appropriate functions by driving imager 14 and/or RFID unit 16 accordingly. For example, the operation of imager 14 and RFID unit 16 may be triggered by serial commands sent to system 10 from a host device 38, or by a hardware button communicating directly with connector 36 or through host device 38. Microcontroller 12 may further be programmed to execute the functions otherwise performed by one or more of image engine 20, RFID transceiver 30, and host transceiver 34, thereby reducing the amount of circuitry and hardware required by system 10.

Figure 3:
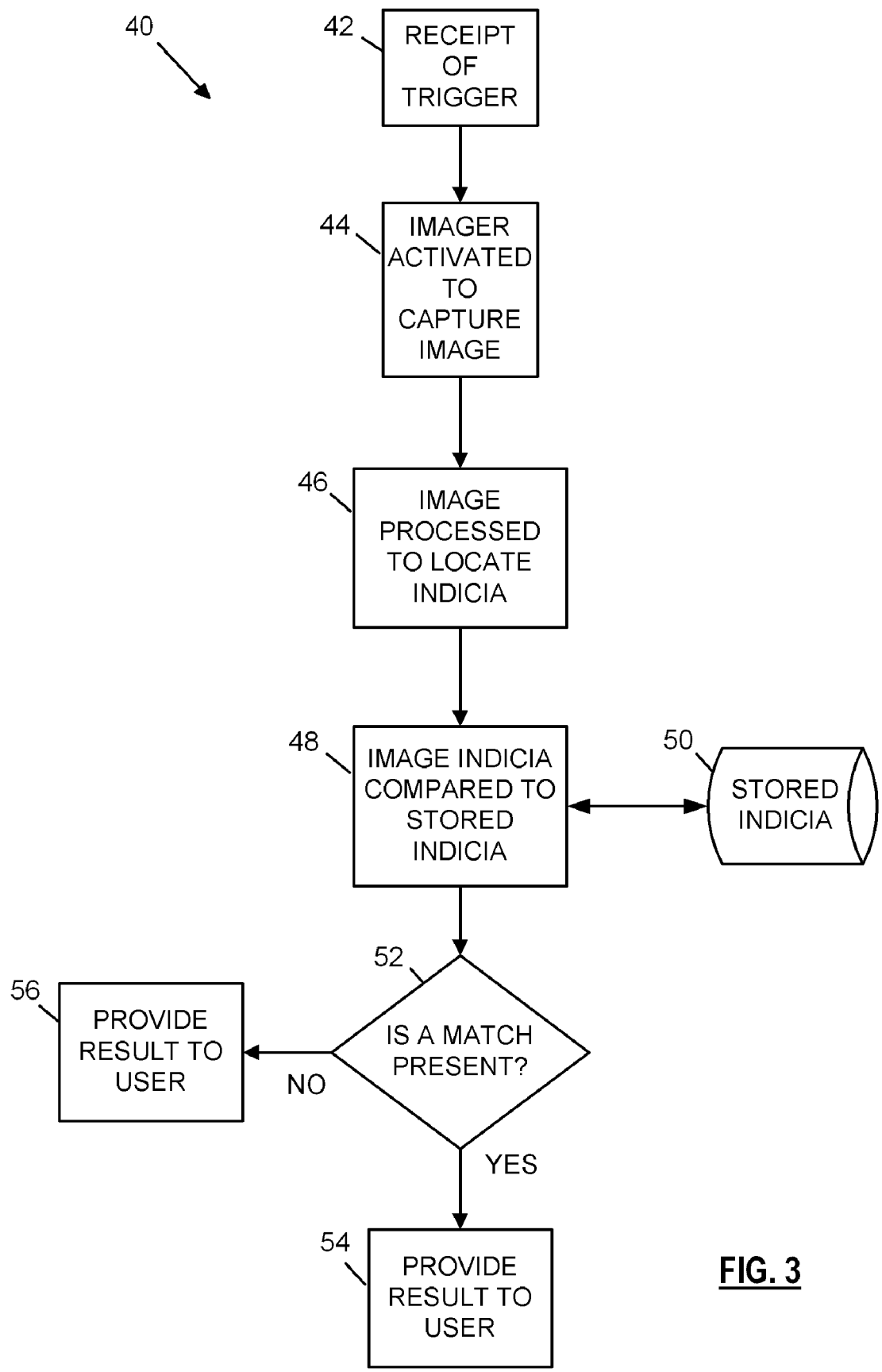
FIG. 3 is a high-level flowchart of a control process according to the present invention.

Referring to FIG. 3, microcontroller 12 is preferably programmed with a logo recognition process 40 for identifying the presence of a particular logo, such as a trademark, in the images captured by imager 14. In general, logo recognition process 40 involves extraction of a target logo, if any, from a captured image and then identification of the extracted target logo as a logo of interest. Template matching is the preferred method to find any form of indicia and may be configured simply by presenting a specimen of a logo or logos of interest to system 10 for initial optical capture and configuration. Using template matching, a template image is used to locate a target logo in an image by computing the similarity between the pre-configured template and the captured image, and by using all of the potential configuration or poses of the template logo. If the similarity between the captured image and the temple is high, a decision may be made that the logo has been detected. This general process may be uses to detect the presence or absence of the indicia, to distinguish between different types of indicia, to determine the location and orientation of the indicia, and to determine how many indicia are present in the image.

More specifically, process 40 begins when system 10 is triggered 42 to capture an image of a target. As explained previously, system 10 may be triggered via a command sent by host device 38 or by a manual trigger connected thereto. Upon receipt of a trigger command at step 42, imager 14 is activated 44 to capture an image in its field of view. The captured image is then processed 46 to determine whether it contains any predetermined logos, such as a trademark or other source identifying indicia. Preferably, a manufacturer trademark or logo is used as the source identifying indicia because it is generally unlawful for an entity to place a trademark belonging to another on a product unless done so with the authority of the trademark owner. Thus, a trademark may be used to verify that a particular device or implement is specifically adapted for and thus acceptable for use with system 10, thereby avoiding the concern that system 10 will unintentionally or intentionally authenticate an unacceptable item presented to imager 14.

Once the image has been processed to determine the presence of one or more predetermined logos at step 46, the predetermined logo is recognized 48. Recognition step 48 preferably comprises comparing the logo against a database 50 of acceptable logos or indicia, or comparing other qualifying criteria against stored date. A check is then performed 52 to determine whether an authorized trademark or logo has been presented, i.e., a "match," is found. If so, the results are provided 54 to the user to communicate the determination that the decision the device in the field of imager 14 is acceptable for use. If a match is not found at step 52, the results are provided to the user 56 to communicate the determination that the device in the field of imager 14 is not acceptable for use. Notification steps 54 or 56 may comprise generating a user cognizable alert locally, such as an attached alarm or light, generating a user cognizable alert, sending a text byte to host device 38, sending a command string to an external device, and like, or any combination thereof. For example, the result may be transmitted through interface 18 to host device 38, which can then take appropriate action, such as disabling or enabling the use of system 10, or refusing to provide power to the item, such as refusing to provide electrical energy to the scalpel in the example of an electrosurgical system that includes an electric scalpel that is interconnected to and powered by a base unit.

The step of determining the presence of a logo 46 generally consists of determining the location of the region of interest, i.e., the region that may contain the logo, in the applicable captured image field, so that the field of interest may be extracted for recognition processing at step 48. Typically, logos such as trademark are used to refer to the source of goods and will be confined to a particular location on an informational panel or label that is isolated from the portion of the media that contains other information, such as a barcode or product description. It should be clear to those of skill in the art that the known dimensions of a label and predetermined location of the logo with respect to the rest of the label may be used to identify the region of interest in a captured image field using preconfigured geometric coordinates. Once the location of the region of interest has been configured, the captured image may be redacted or cropped to remove irrelevant matter, leaving only the region of interest, i.e., the region containing the trademark or logo to be recognized.

Once the particular region of interest has been isolated, the step of recognizing the logo 48 may be implemented. Recognition 48 may comprise any one or more techniques depending on the results of detection and extraction process 46. If the extracted logo in the region of interest does not suffer from geometrical distortion, e.g., altered scale or rotation, the process of normalized correlation may be used to determine the correspondence between a captured image and a previously stored logo or trademark. Normalized correlation is robust to noise, reduced resolution, clutter occlusions, and minor geometric transformations. Depending on the size of the region of interest, a graph of the normalized cross correlation surface of the captured image will identify both the presence of a particular indicia and its location in the region of interest. As normalized correlation is quite complex mathematically and therefore time consuming, matching may be performed using an image pyramid, which is constructed by successively halving the resolution of the image and combining two-by-two blocks of pixels in a higher resolution into a single pixel at the next lower resolution. To improve performance with respect to misaligned indicia, templates may be created in multiple orientations and scales.

In the event that it is possible for the region of interest to undergo severe geometric distortions, normalized correlation may not be effective. In this case, geometric-invariant statistical moments or shape descriptors may be used to recognize the logo. With respect to statistical moments, there are seven two-dimensional moments that are insensitive to translation, scale change, mirroring, and rotations. Any one of these moments, or a combination of more than one, or even all seven moments may be considered to determine whether the captured image logo corresponds to a predetermined logo.

With respect to shape descriptors, curvatures, corners, rounded edges, elongation, or other salient points of the target logo may be considered. Fourier descriptors, boundary signatures, and active contours matching may be used.

Wavelet techniques may also be used to recognize the presence of a predetermined logo or trademark. For example, the horizontal and vertical projections of the logo may be computed, and a wavelet transform applied to low-pass filter the projections. The low-pass wavelet coefficient vector may then be used as a signature of the logo, which can then be compared to one or more stored signatures to recognize the logo.

Negative shapes may also be used to normalize the logo to a binary image and perform a connected component labeling of the logo. The shape feature vector for each component of the logo may then be computed. For example, eccentricity, as measured by the ratio between the length of width of an axis-aligned boundary box, provides a measure of elongation of each component. In addition, circularity, as measured by the ratio of the perimeter of the component of the logo and the perimeter of a circle of equivalent area, may be considered. Rectangularity, as measured by the ratio of the area of the logo component and the area of its bounding box, may further be considered. Finally, a hole area ratio, as measured by the ratio of the area of any holes inside logo components and the area of the solid part of the component, may be considered. Any one or more of these measurements may be determined from the target image and then compared against stored measurements to recognize the logo.

It should be recognized by those of skill in the art that the particular measurement or measurements that are considered may depend on the nature and shape of the logo to be recognized. For example, a generalized Hough transform for matching an object having arbitrary shape may be implemented in recognition step 48. In this process, a reference point is defined and a LUT that defines the relationship between an edge point, its gradient orientation, and the distance to the reference point is built. A LUT may be built by selecting an arbitrary reference point (xref,yref), and for all the points on the edge (xi, yi) construct a line from (xi, yi) to (xref, yref), measure the line ($\beta$i, ri), compute the orientation of the boundary $\Omega$i, and add the result ($\beta$i, ri) to a table indexed by $\Omega$i. When the table is complete, a Hough transform of the image may be performed. The Hough transform is accomplished by computing the point (xref, yref) for each point in the image (xi, yi) using:

$$\begin{cases} x_{ref} = x_i + r_i \cos\beta_i \\ y_{ref} = y_i + r_i \sin\beta_i \end{cases}$$

where (ri,$\beta$i) are derived from the R-table, starting from the orientation of the point $\Omega$i. The Hough space (initial all zero image) is accumulated in (xref, yref) using:

$$A(x_{ref}, y_{ref})++$$

and then searching for local maxima in A to identify the center of the indicia, if any, within the captured image.

What is claimed is:

1. An apparatus for identifying and verifying authenticity of an item, comprising:
   an optical imager;
   a microcontroller interconnected to said imager;
   a database accessible to said microcontroller; and
   wherein said microcontroller further comprises a first module programmed to configure said apparatus prior to verifying the authenticity of said item by capturing a first optical image of at least one indicia and storing at least a portion of said first optical image in said database, a second module programmed to trigger capturing of at least a second optical image when said item is presented to said optical imager, a third module programmed to indentify and extract a predetermined region of interest from said optical image, a fourth module programmed to retrieve said first optical image from said database and compare said first optical image to said region of interest in said second optical image, and a fifth module programmed to determine whether said item is authentic based on said comparison of said fourth module by computing at least one shape feature vector for said indicia and comparing said vector to at least one stored vector.

2. The apparatus of claim 1, wherein said indicia comprises a trademark.

3. The apparatus of claim 2, wherein said fifth module determines whether said item is authentic by additionally performing a normalized correlation between said first optical image and said second optical image.

4. The apparatus of claim 2, wherein said fifth module determines whether said item is authentic by additionally comparing at least one statistical moment in said first optical image and said second optical image.

5. The apparatus of claim 2, wherein said fifth module determines whether said item is authentic by additionally using a wavelet transform to generate a signature based on said indicia and then comparing the signature of said indicia to at least one stored signature.

6. An apparatus for verifying the authenticity of an object, comprising:
an optical imager for capturing an optical image of said item;
a microcontroller interconnected to said imager, wherein said microcontroller further comprises a first module programmed to configure said apparatus prior to verifying the authenticity of said item by capturing a first optical image of at least one indicia and storing at least a portion of said first optical image in said database, a second module programmed to trigger capturing of at least a second optical image when said item is presented to said optical imager, a third module programmed to indentify and extract a predetermined region of interest from said optical image, a fourth module programmed to retrieve said first optical image from said database and compare said first optical image to said region of interest in said second optical image, and a fifth module programmed to determine whether said item is authentic based on said comparison of said fourth module; and
a module configured to enable or disable the use of a device interconnected to said apparatus depending on whether said microcontroller determines the presence of said predetermined indicia.

7. The apparatus of claim 6, further comprising a module configured to send a command indicating the presence or absence of said indicia.

8. The apparatus of claim 7, wherein the command is sent to a device connected to said apparatus.

9. The apparatus of claim 6, further comprising a module configured to provide a user cognizable alert indicating the presence or absence of said indicia.

10. The apparatus of claim 9, wherein the user cognizable alert comprises at least one alert selected from the group consisting of an audible alarm, a light emitting device, a user display screen message, or combinations thereof.

11. The apparatus of claim 6, wherein the device is disabled or enabled by controlling whether the device receives electrical power.

12. A method of ensuring the authenticity of a device, comprising the steps of:
configuring an authentification process by capturing a first optical image of at least one predetermined indicia and storing at least a portion of said first optical image containing said at least one predetermined indicia in a storage medium;
capturing a second optical image of a target;
indentifying and extracting a predetermined region of interest from said second optical image;
retrieving said first optical image from storage medium and comparing said first optical image to said region of interest in said second optical image;
determining whether said item is authentic based on said comparison; and
notifying a user whether the predetermined indicia is present in the image by providing a user cognizable alert.

13. The method of claim 12, wherein the step of capturing an optical image comprises providing a means for trigging image capture and capturing an image in response to activation of said means for triggering image capture.

14. The method of claim 13, wherein the step of determining whether said item is authentic based on said comparison comprises determining whether said region of interest contains data corresponding to data representative of said predetermined indicia in said first image.

15. The method of claim 14, wherein the step of determining whether said region of interest contains data corresponding to data representative of said predetermined indicia comprises comparing said data in said region of interest to said data representative of said predetermined indicia using normalized correlation.

16. The method of claim 14, wherein the step of notifying a user whether a predetermined indicia is present in the image comprises the additional step of enabling or disabling a device depending on whether said predetermined image is present.

17. The method of claim 12, wherein the step of notifying a user whether a predetermined indicia is present in the image comprises the additional step of outputting a command indicating whether said predetermined indicia is present.

* * * * *